United States Patent [19]

Samson

[11] Patent Number: 5,649,978
[45] Date of Patent: Jul. 22, 1997

[54] TEMPORARY INFLATABLE INTRAVASCULAR PROSTHESIS

[75] Inventor: Gene Samson, Milpitas, Calif.

[73] Assignee: Target Therapeutics, Inc., Fremont, Calif.

[21] Appl. No.: 328,532

[22] Filed: Oct. 25, 1994

Related U.S. Application Data

[63] Continuation of Ser. No. 62,449, May 11, 1993.
[51] Int. Cl.⁶ .................................. A61F 2/06; A61F 2/04
[52] U.S. Cl. .................................. 623/1; 623/12
[58] Field of Search .................. 600/31, 36; 623/1, 623/11, 12; 604/95, 96, 97, 98, 99, 100, 101, 102, 103; 606/191–195

[56] References Cited

U.S. PATENT DOCUMENTS

| | | |
|---|---|---|
| 4,183,102 | 1/1980 | Guiset . |
| 4,447,227 | 5/1984 | Kotsanis . |
| 4,706,671 | 11/1987 | Weinrib . |
| 4,762,130 | 8/1988 | Fogarty et al. . |
| 4,820,298 | 4/1989 | Leveen et al. . |
| 4,881,939 | 11/1989 | Newman ........................ 600/31 |
| 4,886,062 | 12/1989 | Wiktor . |
| 4,889,137 | 12/1989 | Kolobow ...................... 606/191 |
| 4,909,252 | 3/1990 | Goldberger . |
| 4,934,786 | 6/1990 | Krauter . |
| 5,000,734 | 3/1991 | Boussignac et al. . |
| 5,007,926 | 4/1991 | Derbyshire . |
| 5,019,093 | 5/1991 | Kaplan et al. .................. 606/228 |
| 5,181,911 | 1/1993 | Shturman ........................ 604/96 |

FOREIGN PATENT DOCUMENTS

WO92/18195  10/1992  WIPO .

*Primary Examiner*—Debra S. Brittingham
*Attorney, Agent, or Firm*—Morrison & Foerster

[57] ABSTRACT

This invention is in the general field of surgical instruments and relates specifically to an inflatable prosthetic device suitable for use in cardiovascular or endovascular procedures, such as angioplasty, to restore normal blood flow through the vessel. The device is generally a helically wound balloon having a false lumen through its center which is inflatable through its integral inflation lumen.

6 Claims, 3 Drawing Sheets

TEMPORARY INFLATABLE INTRAVASCULAR PROSTHESIS

This application is a continuation of application Ser. No. 08/062,449, filed May 11, 1993.

TECHNICAL FIELD

This invention is in the general field of surgical instruments and relates specifically to an inflatable prosthetic device suitable for use in cardiovascular or endovascular procedures,such as angioplasty, to restore normal blood flow through the vessel. The device is generally a helically wound balloon having a false lumen through its center which is inflatable through its integral inflation lumen.

BACKGROUND OF THE INVENTION

Blood vessels within the vasculature of the human body may become diseased due to plaque deposits within the endothelial lining of the vessel wall. Progression of the disease causes narrowing of the vessel segment thus limiting the blood flow across the segment. Ultimately, blood coagulates in the diseased segment causing cellular necrosis in the supply region of the artery, often with fatal results.

A common method of treatment used in restoring normal blood flow through a diseased segment of a blood vessel is balloon angioplasty. As is described in U.S. Pat. No. 4,909, 252, the therapy involves the use of a balloon catheter, that is, a balloon fastened around the exterior of a hollow catheter tube. The balloon is placed across the diseased vessel segment and is inflated with sufficient pressure to cause the deposit to compress against the vessel wall.

The above method of intervention, using conventional balloon catheters, causes a complete interruption of blood flow of the vessel while the balloon is pressurized. This blood flow interruption limits the inflation duration of the balloon. Keeping the balloon inflated for an extended period causes a risk of damage to the region nourished by the vessel—a region likely already weakened by insufficient blood supply. Ideally, the situation calls for a device that will compress the deposit against the artery wall for an extended period while maintaining a sufficient flow of blood through the segment. To offset the limitation of the current conventional devices, a repeated cycle of balloon positioning, balloon inflation, balloon deflation, balloon withdrawal from the diseased segment, and fluoroscopic determination of lumen enlargement of the dilated site is performed until sufficient blood flow is restored. This method is tedious, time consuming, cumbersome to the physician and inconvenient to the patient.

As an alternative to a conventional balloon catheter, U.S. Pat. No. 4,909,252 describes a perfusion balloon catheter that allows passage of blood even when the balloon is fully inflated. The cylindrical balloon is substantially donut shaped in cross-section and permits the flow of blood through the blood vessel.

Another type of balloon catheter is described in U.S. Pat. No. 4,762,130. That catheter has a corkscrew-like balloon that can be inflated, reportedly without possible perforation or abrasion of the vessel wall.

A similar device is shown in WO 92/18195, to Shturman et al. The device shown there involves a thin walled, helically coiled balloon suitable for use as an angioplasty catheter. The successive turns of the coil are joined by an adhesive, by longitudinal straps, or by wire.

The current invention involves the use of an inflatable intravascular prosthesis to restore normal blood flow to a diseased vessel. Unlike the balloon catheters described above, the prosthesis is a helically wound polymeric tube, the coil turns preferably secured using longitudinal or helical strips of polymer. The prosthesis is adapted to remain in place inside the blood vessel until normal blood flow resumes and may then be removed. More permanent uses for intravascular stents are known in the art. U.S. Pat. No. 4,820,298 describes the use of an internal vascular prosthesis for clotting and ingrowth of tissue to seal off an aneurysm. The prosthesis is a single helix of thin-walled, elliptical tubing that assumes a natural spiral configuration when released into the vessel. No mention is made of a temporary prosthesis for use in opening a vessel and supporting the vessel wall during angioplasty procedures. Such is also true for copending U.S. patent application Ser. No. 07/011,480 filed 26 Jan. 1993, directed to an endovascular inflatable stent for use in the treatment of aneurysms, diseased blood vessels and other bodily lumen.

In addition to plaque deposits in the blood vessel, restriction of normal blood flow through a segment of the vasculature can be due to other causes. Narrowing of the artery lumen can be caused by vascular spasms. Spasm has been well documented for example, on the segment of an artery proximal in which an aneurysm has been clipped. For this type of clinical case, prolonged dilation of the narrowed segment is highly desirable. A temporary prosthesis that will support the arterial wall and allow sufficient blood flow is a preferred mode of therapy. The temporary prosthesis of the present invention can be kept in place for an extended period of time and be removed once the spasm has subsided.

SUMMARY OF THE INVENTION

The present invention is a catheter assembly for use in conjunction with an angioplasty procedure or interventional therapy for vascular spasm. The assembly comprises an elongate polymeric catheter body having a proximal end and a distal end and a central lumen passing from the proximal end to the distal end. The catheter body further comprises an inflation lumen that is generally coaxial and colinear with the central lumen, the inflation lumen passing from the proximal end and communicating with an inflatable tip. The inflation lumen is located proximally to the catheter body distal end and has a proximal and a distal end. The distal end of the inflatable tip is a helically wound tubing section that is generally colinear with the inflation lumen of the catheter body. The inflatable tip proximal end is adapted for fluid communication with the inflation lumen and the inflatable tip distal end is sealed. The inflatable tip may be inflated and deflated.

In a second variation, the invention is an inflatable vascular prosthesis. The prosthesis comprises an elongate tube having a proximal and a distal end, with a lumen extending from the proximal end to the distal end and closing at that distal end. The distal portion of the tube is wound into a helix to form a secondary lumen within the helix having a deflated outside diameter and a larger inflated outside diameter.

DETAILED DESCRIPTION OF THE INVENTION

The invention device is an inflatable prosthetic device suitable for temporary placement in any body lumen, but primarily in a vascular lumen. It is made of two critical portions—an inflatable tip having a lumen along its axis and an inflation lumen or shaft. The inflatable tip is also deflatable and is made of a simple, helical winding of polymeric tubing which is held in the helical configuration by tie strips which adhere to the tubing and "tie" it into the desired inflated shape. The inflation lumen or shaft carries and removes inflation fluid from the helical inflatable tip.

Figure 1:
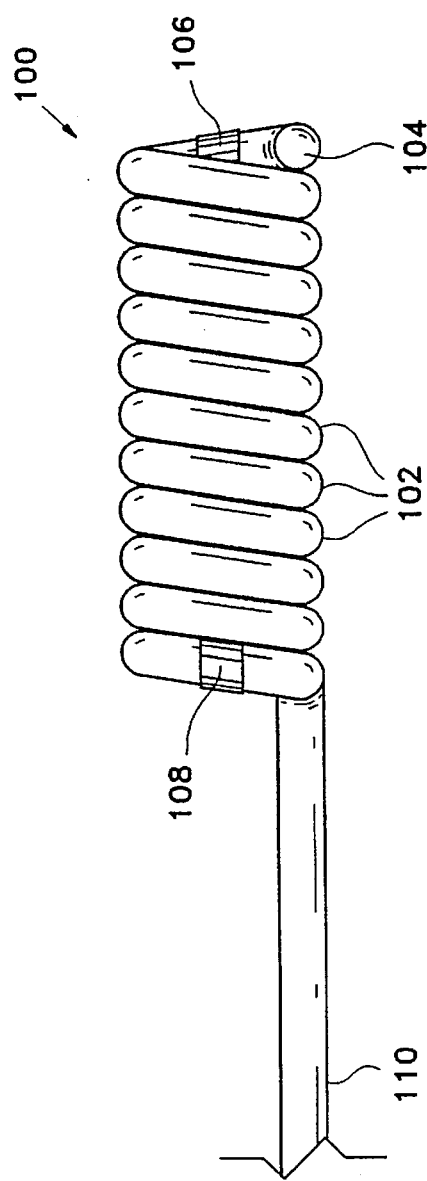
FIG. 1 is an enlarged sideview of a variation of the inventive prosthesis.

FIG. 1 shows an enlarged side view of one variation of the prosthetic device (100). In this variation the polymeric coils (102) are tightly wound, that is, the pitch of the coil is the same as the diameter of the polymeric tubing making up the coil. The outside diameter of the coil may be as much as five times the size of the diameter of the polymeric material or may be folded or compressed such that the outside diameter of the coil is no greater than about twice the outer diameter of the inflation lumen or shaft.

In the variation shown in FIG. 1, there are no tie strips. The coil shape is maintained by causing the coil turns to adhere to each other. This adherence may be accomplished by choosing a polymer which after winding of the coil, may be heat treated to allow adjacent coils to stick to each other. The distal end of the polymeric tube making up the inflatable column is closed (104) by crimping the tubing and/or plugging it with a thermoplastic filler or the like. A radiopaque marker (106) may be placed at the distal end and one (108) at the proximal end of the column. These markers are suitable for proper placement of the prosthesis prior to inflation and may be any suitable radiopaque material, preferably metal. Materials such as the platinum series of metals (platinum, palladium, etc.) and gold, silver, and tantalum may be used as these markers. Certain stainless steels are also suitable for use as markers. Alternatively, the polymer used in the catheter body may be radio-opaque or made so by addition of a filler such as barium sulfate, bismuth trioxide, bismuth carbonate, tungsten, tantalum, or the like.

The inflation lumen or shaft (110) in this variation is common to the polymeric tubing making up the coils (102).

Figure 2:
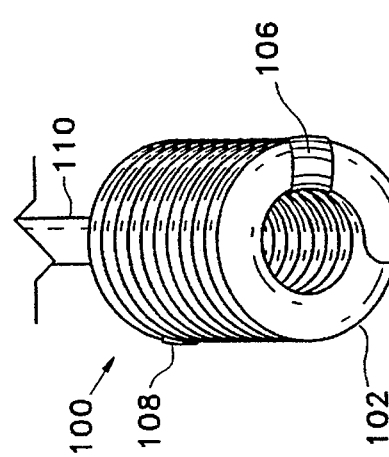
FIG. 2 is an enlarged end view of the prosthesis shown in FIG. 1.

FIG. 2 is an enlarged end view of the prosthesis found in FIG. 1. The various coils (102), distal end plug (104), and distal radiopaque marker (106) may be seen.

Figure 3:
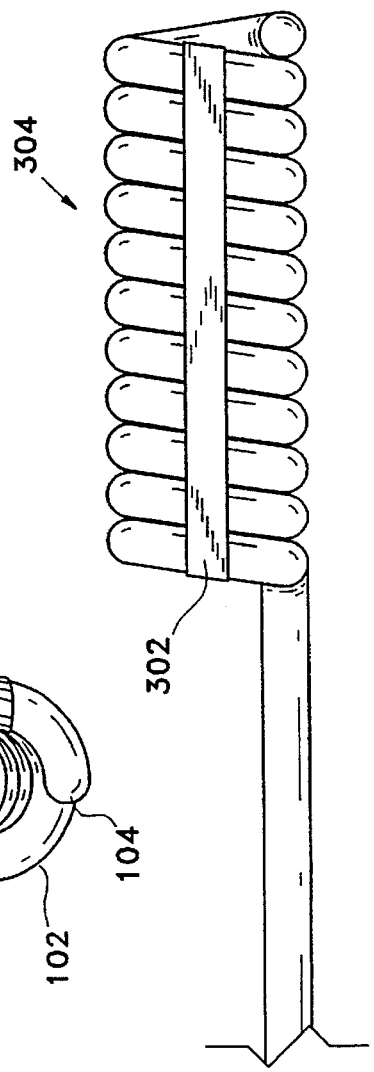
FIG. 3–6 are enlarged sideviews of variations of the inventive prosthesis.

FIG. 3 shows a variation of the invention device similar in design to that shown in FIGS. 1 and 2 but using a sizing strip (302). Sizing strips may be placed outside the helical column (304) as is shown in FIG. 3 and may be placed inside the lumen of the column. They may be used in conjunction with or instead of the adhesive methods discussed in relation to FIG. 4.

The polymeric tubing making up the helical tip of each of the variations discussed above and below desirably is made of material which is relatively inelastic. That is to say, the coil inflates to a specific size when filled with an inflation fluid, but does not inflate further or "balloon". Elastomeric prostheses that further inflate become somewhat inflexible and do not follow vascular curves very readily.

Preferred polymers for the tubing include polyolefins such as high and low density polyethylene, polypropylene, and polybutylene as well as mixtures and interpolymers of these materials. Other suitable polymers include polyacrylonitrile, polyurethanes, polyethylene terephthalate and polybutylene terephthalate, and "TEFLON" (tetrafluoroethylene). These materials are substantially bioinert or, at least, biocompatible. An especially suitable tubing is made of polyethylene having a melting point of about 350° F. Such polyolefins may be "hardened" through the use of irradiation if so desired.

The sizing strips may be of the same polymeric materials or others of appropriate physical characteristics. Especially suitable are the polyolefins listed above. The sizing strips may be glued to the helical tubing or made to adhere to the tubing in some other fashion. For instance, if a tubing have a high melting temperature is used for the helical column, sizing strips of a lower melting temperature may be used. Placement of the sizing strips against the tubing in a configuration such as shown herein, and heat treated at a temperature between the heat indices of the two polymers. The sizing strips will deform and adhere to the tubing holding it in place.

Figure 4:
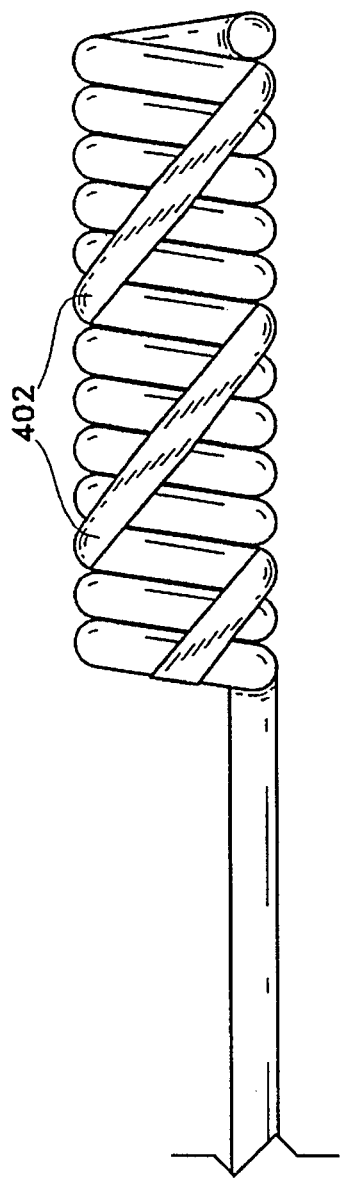

FIG. 4 shows another variation in which the sizing strips (402) are placed helically about the column. As with the variations discussed above, the strips may be placed either (or both) inside and outside the column. It is desirable that the helix formed by the sizing strips be of an opposite "handedness" to that of the tubing helix. In this way, the sizing strips maintain the shape of the column upon inflation. If the sizing strips are wound in the same direction, the coil will show a modest tendency to unwind upon inflation. As will be discussed below, in certain circumstances, a diameter increase may be desirable.

Figure 5:
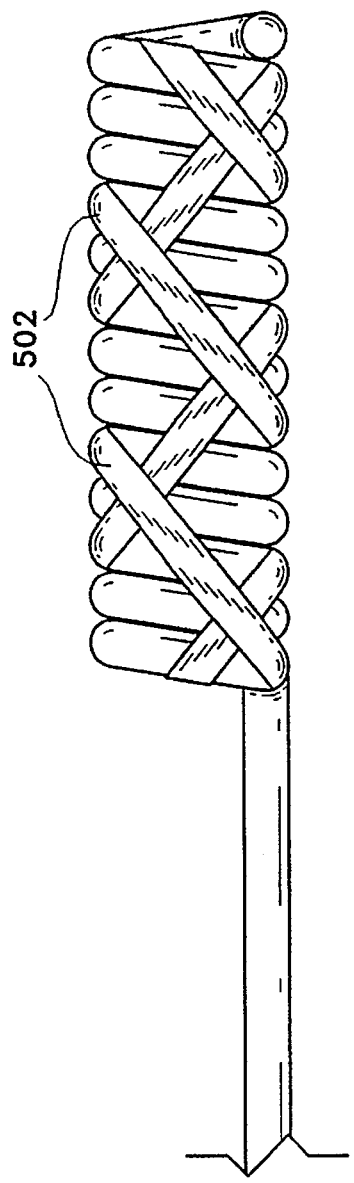

FIG. 5 shows a variation in which the sizing strips (502) cross in a helical fashion. This variation usually has the least axial flexibility of all of those discussed above.

As may be apparent from the above discussion of the structures of the variations, each of the variations will have more or less compliance or flexibility depending, in major part, on the number and placement of the sizing strips. For instance, the FIGS. 1 and 2 variation has moderate flexibility when the coils adhere to each other. The FIG. 3 variation, using only an inside or outside sizing strip, will have significant compliance with the interiors of various body lumens. That is to say that the FIG. 3 variation could be adopted to form a "C" shape prosthesis when placed in a region where, for instance, an artery makes a large curve. The prosthesis region on the outside of the coil, as placed, will have gaps between the coil windings. The compliance for the remainder of the variations should be apparent.

The coil column need not be tightly wound, as has been shown in the figures discussed above. Depending in large measure upon the use to which the prothesis is placed, the coil column need not be liquid tight. Obviously, if the column coil is wound with a pitch greater than the diameter of the tubing—see, for instance, FIG. 6—there will be gaps between the adjacent coils. When treating vascular spasms, a long prothesis applying a gentle pressure over a significant distance of the vessel lumen may be desirable.

Figure 6:
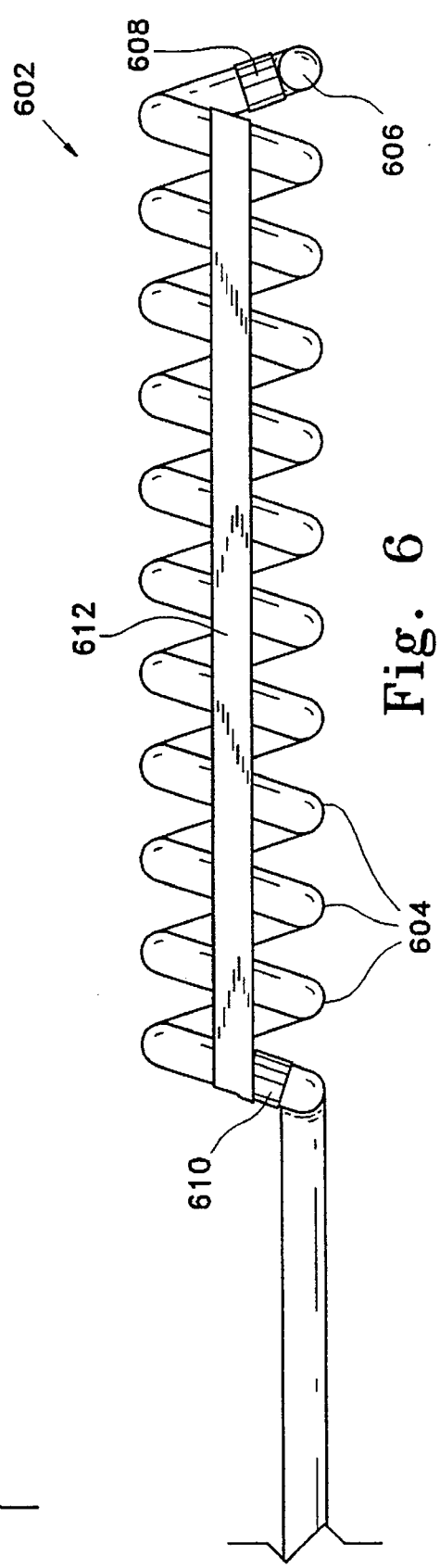

FIG. 6 shows a side view of a variation (602) of the invention similar in most respects to the tightly wound version (304) shown in FIG. 3. The coils (604) are, however, not tightly wound. The distal end of the column is plugged (606). A distal radiopaque marker (608) and a proximal radiopaque marker (610) are also present. A sizing strip (612) is shown as placed on the outside of the column.

Figure 7:
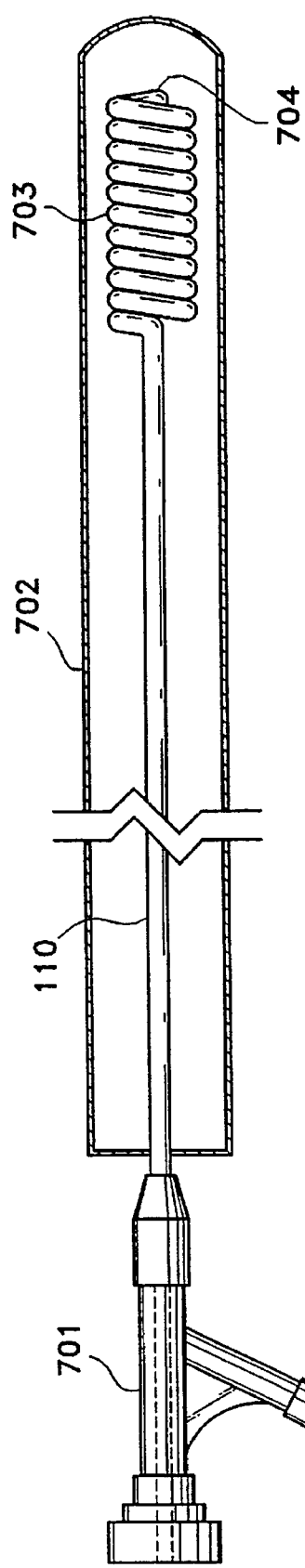
FIGS. 7 and 8 are enlarged sideview of variations of the inventive catheter assembly.
Figure 8:
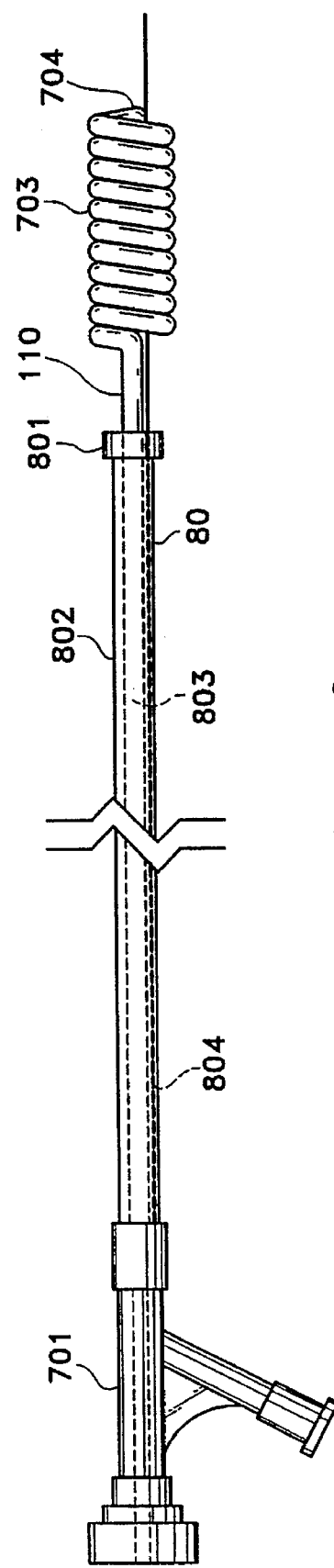

As is evident from the above discussion, FIGS. 1–6 show the inventive prosthesis in their inflated state. The device is inserted into and removed from the vasculature in its uninflated state, as indicated in FIGS. 7 and 8.

The other variations discussed above, e.g., sizing strips placed inside the column lumen, multiple sizing strips, crossed sizing strips, etc., are all applicable to the open wind version discussed here.

The inventive device may be used as a portion of a single lumen or a double lumen catheter assembly. For a single lumen catheter assembly, the proximal end of the inflation lumen or shaft (e.g., 110 in FIG. 7) is fitted with a conventional fitting (701) to allow attachment to an inflation device, such as a syringe, preferably having a pressure indicator. The inventive device may be delivered within a guiding catheter (702) that coaxially surrounds the invention device, the helically wound coil (703) being in its relaxed, folded, or crushed configuration. The catheter assembly is maneuvered into position in the body lumen prior to inflation. A guidewire may be inserted through the guiding catheter (702) and the false lumen (704) of the helical coil to aid in guiding the catheter assembly to the target site. The proximal end fitting (701) is then attached to the end of the inflation lumen (110). The prosthesis is then inflated such that the walls of the targeted vessel are supported yet blood is allowed to flow through the lumen (704) of the distal helically wound portion (703). When the procedure is completed, the device may be deflated by applying vacuum to the proximal end fitting (710) and the device removed.

Similarly, the invention device may be used in a double lumen catheter assembly. In this instance, the coil column (110) would include an attachment (801) adapted to attach the coil column (110) to the distal end of the catheter (802) in such a way that the lumen of the coil column (110) is generally colinear with the inner catheter lumen (803). In this configuration, the outside diameter of the coil is the size of the outside diameter of the catheter, or greater, usually about 20% greater.

A guidewire (804) may be inserted through the catheter outer lumen (805) and the false lumen of the helically wound coil (704). The guidewire (804) is then used to maneuver the collapsed catheter assembly to the desired target site. The guidewire (804) is then removed and an inflation device attached to the proximal end fitting (701). The prosthesis is inflated such that the walls of the targeted vessel are supported yet blood is allowed to flow through the lumen (704) of the distal helically wound portion (703). When the procedure is completed, the device may be deflated by withdrawing the included liquid from the proximal end fitting (701). The entire device may then be removed.

The embodiments shown and described above are only exemplary. Various modifications can be made in the construction, material, and arrangement and still be within the scope of the invention found below in the claims.

I claim as my invention:

1. An inflatable vascular prosthesis comprising:
   an elongate tube having a proximal and a distal end, an outer diameter, a lumen extending from the proximal end to the distal end, said lumen closing at said distal end, wherein at least a part of said elongate tube adjacent the distal end is wound into a helix to form an inflatable tip having a secondary lumen within the helix, where the helix is maintained in a helically wound configuration with polymeric tie strips helically wound about the inflatable tip and which adhere to the helix and where said helix has a deflated outside diameter and a larger inflated outside diameter and where the helix is both inflatable and deflatable.

2. The prosthesis of claim 1 wherein the inflatable tip is compressed to form a compressed inflatable tip having an outside diameter no greater than about twice the outer diameter of the elongate tube.

3. The prosthesis of claim 1 where the helix has a proximal and a distal end and has a radiopaque marker at least at the distal end.

4. The prosthesis of claim 1 where the helix has a radiopaque marker at both the proximal and distal ends.

5. The prosthesis of claim 1 where the tubing is wound in adjacent turns making up the helix and the adjacent turns are fused to form the helix.

6. The prosthesis of claim 1 where the tubing is wound in adjacent turns making up the helix and the adjacent turns are partially fused to form the helix.

* * * * *